(12) United States Patent
Smith

(10) Patent No.: US 7,049,478 B1
(45) Date of Patent: May 23, 2006

(54) TRI-LOBE PLANAR HEEL WOUND DRESSING

(76) Inventor: Patricia Ann Smith, 405 Swann Dr., Midfield, AL (US) 35228

( * ) Notice: Subject to any disclaimer, the term of this patent is extended or adjusted under 35 U.S.C. 154(b) by 0 days.

(21) Appl. No.: 11/046,971

(22) Filed: Jan. 31, 2005

Related U.S. Application Data

(60) Provisional application No. 60/553,332, filed on Mar. 16, 2004.

(51) Int. Cl.
*A61F 5/00* (2006.01)

(52) U.S. Cl. ............................ 602/42; 602/43; 602/54; 602/58; 128/892; 128/893

(58) Field of Classification Search .................. 602/42, 602/43, 54, 55, 58; 128/888–889, 892–894; D24/189, 190, 191, 192
See application file for complete search history.

(56) References Cited

U.S. PATENT DOCUMENTS

| | | | | |
|---|---|---|---|---|
| 2,082,503 A | * | 6/1937 | Meadows | 450/57 |
| 2,505,458 A | * | 4/1950 | Brauer | 450/57 |
| 3,011,494 A | | 12/1961 | McGowan | 128/892 |
| 3,234,941 A | * | 2/1966 | Tucker | 128/888 |
| 3,357,425 A | * | 12/1967 | Morgan | 602/41 |
| 3,508,544 A | * | 4/1970 | Moore et al. | 128/892 |
| 3,530,598 A | * | 9/1970 | Kamborian | 36/68 |
| 3,670,725 A | * | 6/1972 | Gaylord, Jr. | 128/892 |
| 4,736,477 A | * | 4/1988 | Moore | 5/648 |
| 4,762,123 A | * | 8/1988 | Dedo | 128/898 |
| 5,820,578 A | * | 10/1998 | Johansen | 602/57 |
| 5,827,213 A | | 10/1998 | Jensen | 602/62 |
| D404,134 S | * | 1/1999 | Dunshee | D24/189 |
| D405,884 S | * | 2/1999 | Roper | D24/192 |
| 5,919,180 A | * | 7/1999 | Raimondo | 604/387 |
| D480,144 S | * | 9/2003 | Adams et al. | D24/189 |
| 6,664,435 B1 | * | 12/2003 | Masini | 602/58 |
| 2003/0139697 A1 | | 7/2003 | Gilman | 602/54 |
| 2003/0225356 A1 | | 12/2003 | Kulichikhin et al. | 602/54 |
| 2004/0049146 A1 | * | 3/2004 | Kolte et al. | 602/61 |

OTHER PUBLICATIONS

Oxford Online Dictionary, definition of "major", printed Jan. 31, 2006.*

* cited by examiner

*Primary Examiner*—Henry Bennett
*Assistant Examiner*—Amanda Wieker
(74) *Attorney, Agent, or Firm*—Kenneth M. Bush; Gerald M. Walsh; Bush IP Law Group, LLC

(57) ABSTRACT

A planar wound dressing for the heel of the foot, having an adhesive layer with a backing layer, and three slits which can be reversibly closed and joined to form a non-planar wound dressing that conforms to and adheres to the heel of the foot. The wound dressing is constructed so that one slit is placed over the Achilles tendon, the second slit is placed over the inner ankle, and the third slit is placed over the outer ankle. With this orientation after closure of the slits the wound dressing covers the heel uniformly without wrinkles, gaps, leakage, contamination, or infection. The wound dressing is particularly useful in protecting and preventing blisters on the heel that occur in sports such as soccer, track, and the like.

1 Claim, 1 Drawing Sheet

TRI-LOBE PLANAR HEEL WOUND DRESSING

CROSS-REFERENCE TO RELATED APPLICATIONS

This application claims the benefit of previously filed U.S. provisional patent application Ser. No. 60/553,332 to Patricia Ann Smith, filed Mar. 16, 2004, entitled "THE CLOVER HEEL WOUND DRESSING," incorporated herein by reference.

BACKGROUND OF THE INVENTION

1. Field of the Invention

The present invention is related to adhesive wound dressings, and, more particularly, to planar adhesive wound dressings that become non-planar to conform to the shape of the heel by using slits that cover the ankles and Achilles tendon.

2. Technical Background

The use of planar bandages for use on non-planar surfaces is well established because of the ease of packaging and application of planar bandages. Slits have been used in planar bandages to provide a means for converting the planar bandage into a non-planar bandage which conforms to the surface of a joint such as a heel or elbow. The edges of the slits are pulled together and joined to make a continuous non-planar dressing. Slits have not been useful because they are associated with wrinkling, buckling, leakage, detachment and contamination. These undesired effects result from the inability of slits to adapt to sharply curved contours and changes in contours as a joint is flexed. One effort to overcome these problems was the use of pleats instead of slits. However, the construction of planar bandages to form pleats is relatively complex, and the formation of the pleat in application can also be complex. In addition, the pleat extends out from the dressing and may cause discomfort when wearing a shoe if the dressing is applied to the heel. What is needed, therefore, is a planar wound dressing using durable effective slit closures for application to the heel.

SUMMARY OF THE INVENTION

The present invention is a planar wound dressing for the heel of the foot having an adhesive layer with a backing layer. The planar wound dressing has three slits which can be closed and joined to form a non-planar wound dressing that conforms to and adheres to the heel of the foot. The wound dressing is constructed so that one slit is placed over the Achilles tendon, the second slit is placed over the inner ankle, and the third slit is placed over the outer ankle. With this orientation after closure of the slits the wound dressing covers the heel uniformly without wrinkles, gaps, or leakage. The adhesive characteristics of the wound dressing cause the wound dressing to adhere reversibly to the skin and isolate the wound, thereby promoting wound healing and preventing infection. Because of the simplicity of the slit construction the slits can be repeatedly opened to inspect the wound and then reclosed.

An advantage of the present invention is a one-piece easy to apply planar self-adhering wound dressing for the heel of the foot.

Another advantage is a long lasting wound dressing for the heel that can be covered with socks and shoes.

Another advantage is a wound dressing that can be opened and closed repeatedly for inspection of the wound.

Another advantage is a planar wound dressing for the heel that is simple and inexpensive to manufacture.

Another advantage is a planar wound dressing that protects and prevents blisters on the heel that occur in sports such as soccer, track and the like.

DETAILED DESCRIPTION OF THE PREFERRED EMBODIMENTS

While the following description details the preferred embodiments of the present invention, it is to be understood that the invention is not limited in its application to the details of construction and arrangement of the parts illustrated in the accompanying drawings, since the invention is capable of other embodiments and of being practiced in various ways.

Figure 1:
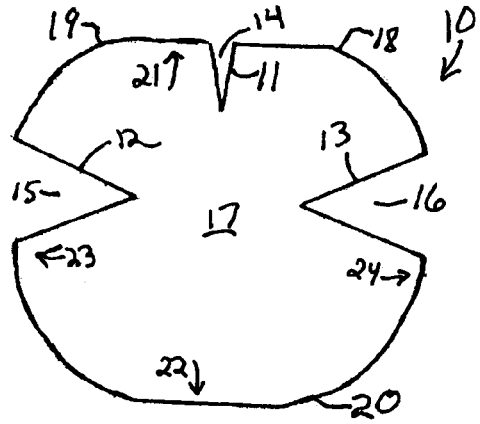
FIG. 1 shows a top plan view of the planar heel wound dressing of the present invention.

FIG. 1 shows a top plan view of the planar wound dressing 10 for the heel of the foot. The dressing 10 has a round or oval shape, with an upper end 21, a bottom end 22, a left side 23, and a right side 24. Upper end 21 has a first slit 11 forming triangular opening 14. Left side 23 has a second slit 12 forming triangular opening 15. Right side 24 has a third slit 13 forming triangular opening 16. Slits 11 and 13 form a first minor lobe 18. Slits 11 and 12 form a second minor lobe 19. Slits 12 and 13 form a major lobe 20.

The three lobes 18, 19, and 20 create a clover leaf appearance to the planar wound dressing 10.

Figure 2:
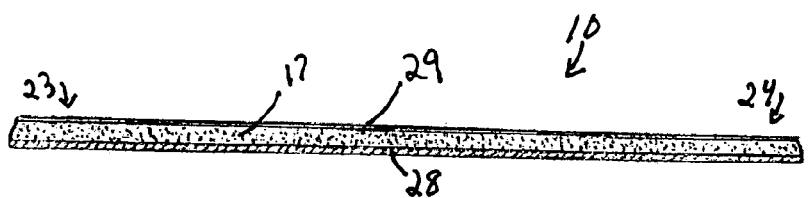
FIG. 2 shows a cross-section view of the planar heel wound dressing.

FIG. 2 shows an end views of planar wound dressing 10. Wound dressing 10 has an adhesive layer 17 with a backing layer 28 on one side and a release cover 29 on an opposite side. Adhesive layer 17 has one or more absorbable hydrocolloids. Backing layer 28 is formed of a layer of elastomeric material such as, for example, polyurethane. The release cover 29 may be composed of paper or plastic that is reversibly bonded to the adhesive layer 17. The release cover 29 protects the surface of the adhesive layer 17 prior to use, at which time it is peeled off and discarded. Numerous compositions are known in the art for the construction of adhesive wound dressings, backings for adhesive wound dressings, and release covers for wound dressings and are suitable for the present invention. Some of these are disclosed in U.S. Pat. No. 5,827,213 and U.S. Patent Application 2003/0225356, which are incorporated herein by reference. Preferred adhesive wound dressings are Allevyn™ from Smith & Nephew, Largo, Fla., and Elasto-Gel™ from Southwest Technologies, Inc., North Kansas City, Mo.

Figure 3:
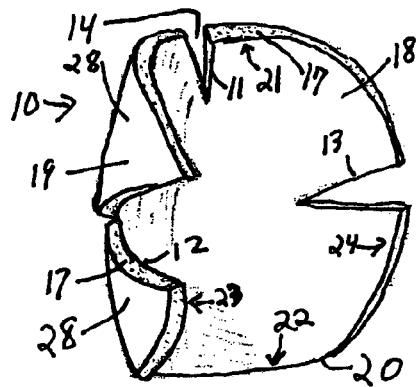
FIG. 3 shows a perspective view of the heel wound dressing with partial closure of the slits to form a non-planar wound dressing.
Figure 4:
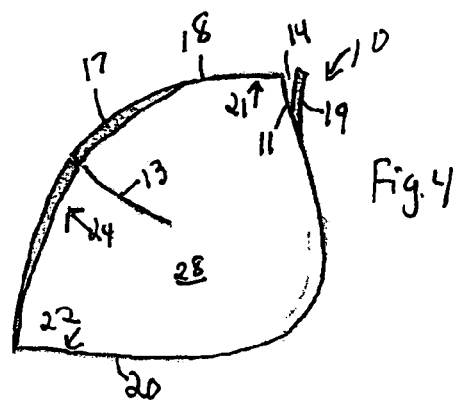
FIG. 4 shows the wound dressing with the slits closed to form a non-planar dressing that conforms to the shape of the heel.

FIG. 3 shows the planar wound dressing 10 with the slits 11, 12, and 13 partially closed so that the wound dressing 10 begins to take a non-planar shape. FIG. 4 shows wound dressing 10 with the slits 11, 12, and 13 closed so that wound dressing 10 conforms to the shape of the heel of the foot. Closure of slit 11 joins the two minor lobes 18 and 19. Closure of slits 12 and 13 join major lobe 20 to minor lobes 18 and 19.

Figure 5:
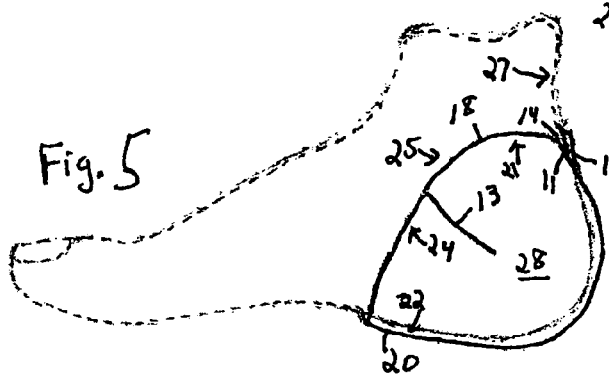
FIG. 5 shows the wound dressing in place on the heel viewed from the inside ankle.
Figure 6:
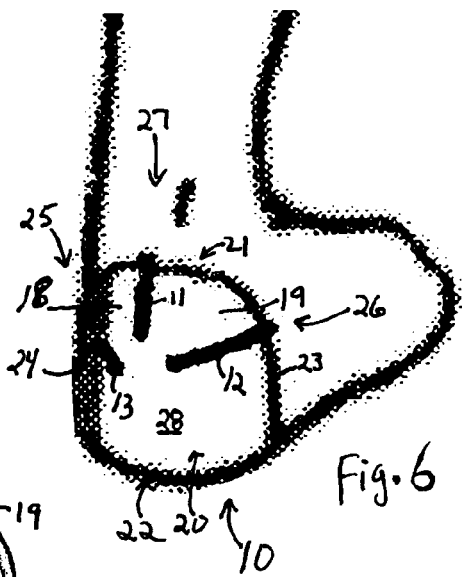
FIG. 6 shows the wound dressing in place on the heel viewed from the back of the heel.

FIG. 5 shows the wound dressing 10 in place on the heel viewed from the inner ankle 25. FIG. 6 shows the wound dressing 10 in place on the heel viewed from the Achilles tendon 27 and the outer ankle 26. Slit 11 fits over the Achilles tendon 27; slit 13 and lobe 18 fit over the inner ankle 25; slit 12 and lobe 19 fit over the outer ankle 26; and major lobe 20 covers the bottom of the heel. Consequently, wound dressing 10 is highly effective in uniformly covering the heel without the formation of wrinkles, gaps, detachments, leaks or contamination.

In order to apply the planar wound dressing 10, release cover 29 is removed from the adhesive wound dressing layer 17. First slit 11 is closed by bringing the edges of the slit together and upper end 21 is placed against the Achilles tendon 27, pressing the adhesive layer 17 against the skin. Bottom end 22 is placed under the heel pressing the adhesive layer 17 against the skin. The edges of the second slit 12 are brought together closing the left side 23, and the adhesive layer 17 is pressed against the skin of the ankle. The edges of the third slit 13 are then brought together closing the right side, and adhesive layer 17 is pressed against the skin of the opposite ankle. The adhesive layer adheres reversibly to the skin of the heel, keeping the slits closed and keeping the wound dressing in place on the heel. The placement of the slits 12 and 13 and minor lobes 18 and 19 over the ankle, prevents the slits from opening as the dressing is used while walking and standing. The surface over these areas has relatively little movement so there is little stress on the closed slits.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, the planar wound dressing may be made in various sizes to accommodate men, women, and children. The slits may be opened to inspect the wound and reclosed as often as needed. The adhesive layer can contain medications. In its planar form the heel wound dressing can be provided in any type of suitable packaging.

It will be understood that various changes in the details, materials, and arrangements of the parts which have been described and illustrated above in order to explain the nature of this invention may be made by those skilled in the art without departing from the principle and scope of the invention as recited in the following claims.

I claim:

1. A method for applying a tri-lobe planar wound dressing to the heel of a foot, said dressing comprising a backing layer, an adhesive layer, an upper V-shaped slit formed along the top of said dressing and a lateral V-shaped slit formed along each opposing side of said dressing such that said dressing comprises a major lobe below said lateral V-shaped slits and two minor lobes above said lateral V-shaped slits, said method comprising the steps of:

a) removing a protective cover from said adhesive layer of said dressing;
   b) bringing the edges of said upper V-shaped slit together in a non-overlapping manner over the Achilles tendon to join said minor lobes together and pressing said minor lobes against the skin to reversibly adhere said minor lobes to the inner and outer ankle with said upper slit superjacent the Achilles tendon; and
   c) bringing the edges of said lateral slits together in a non-overlapping manner over the sides of the heel to join said major lobe to said minor lobes and pressing said major lobe against the skin to reversibly adhere said major lobe to the lower portion of the heel.

* * * * *